United States Patent [19]

Batcheler et al.

[11] Patent Number: 4,514,722
[45] Date of Patent: Apr. 30, 1985

[54] DOMESTIC AUTOMATIC CONTINUOUSLY MONITORING SOIL MOISTURE MONITOR/INDICATOR

[76] Inventors: Jerry H. Batcheler, 1364 Keoncrest Ave., San Jose, Calif. 95110; Raymond G. Marek, 1242 Willo Mar Dr., San Jose, Calif. 95125

[21] Appl. No.: 495,667

[22] Filed: May 18, 1983

[51] Int. Cl.³ .............................................. G08B 21/00
[52] U.S. Cl. ................................ 340/604; 324/65 R; 324/65 P
[58] Field of Search ............... 340/602, 604, 616, 617, 340/620; 324/61 QL, 61 C, 65 R, 65 P; 73/73; 200/61.05

[56] References Cited

U.S. PATENT DOCUMENTS

| | | | |
|---|---|---|---|
| 1,875,359 | 9/1932 | Suits et al. | 340/604 X |
| 2,043,241 | 6/1936 | Eyer | 340/604 X |
| 2,076,441 | 4/1937 | Berry | 340/604 X |
| 2,611,643 | 9/1952 | Higgins | 340/604 X |
| 2,812,976 | 11/1957 | Hasenkamp | 340/604 X |
| 3,882,383 | 5/1975 | Matlin | 340/604 X |
| 3,927,370 | 12/1975 | De Bough | 340/604 X |
| 3,944,916 | 3/1976 | Tillander | 340/604 X |
| 4,020,417 | 4/1977 | Brehob et al. | 340/602 X |
| 4,268,824 | 5/1981 | Phillips | 340/602 X |
| 4,297,686 | 10/1981 | Tom | 340/604 |

OTHER PUBLICATIONS

Radio Electronics (USA), vol. 52, No. 1, Jan., 1981, New Ideas, "Plant Water Gauge" by Bob Mostafapour, p. 73.

Elektor, vol. 2, No. 11, pp. 1121–1123, Nov., 1976, "Dew Line".
Electronics Australia, vol. 37, No. 9, pp. 42–43, Dec., 1975, "Build Our Water Warbler for Healthy Pot Plants" by D. Edwards.

Primary Examiner—James L. Rowland
Assistant Examiner—Daniel Myer

[57] ABSTRACT

The domestic and commercial automatic soil moisture indicator of the present invention employs a pair of probes which are conductive traces (e.g. a printed circuit board) that are coated with material for corrosion and electrolysis resistance to enable long term residence in potted plant soil. The device provides alternating short pulses across the probes to further enhance near zero electrolysis and increase potted plant soil residence time without probe wear. It has a single light emitting diode indicator lamp to blink every ten seconds when soil drops below a customer set level, and a beeper (e.g. piezoelectric ceramic) to sound a beep in unison with the LED flashing during dry soil indication as well as a calibrated-numbered user adjustment to set the dry soil indication level. A coil operating with an integrated circuit DC to DC converter functions to yield operation from a small battery to keep the overall unit small and electric drain down.

Consequently, the unit of the present invention becomes the "state-of-the-art" in soil moisture indicators due to its small size, long battery and electrode life, continuously automatic plant soil moisture monitoring and indication, and compact functionality due to functions integrated into an integrated circuit.

15 Claims, 2 Drawing Figures

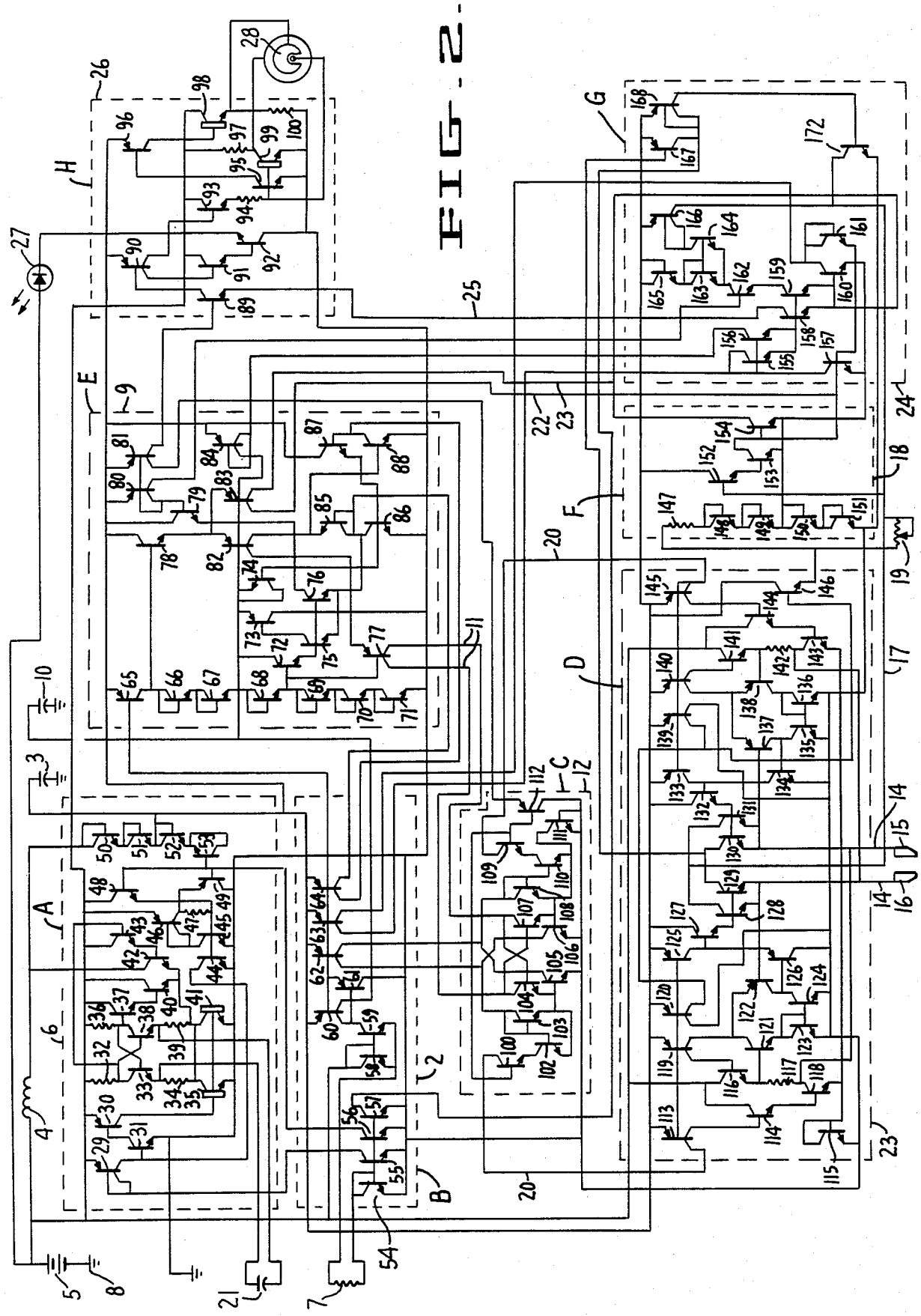

4,514,722

DOMESTIC AUTOMATIC CONTINUOUSLY MONITORING SOIL MOISTURE MONITOR/INDICATOR

SUMMARY OF THE INVENTION

An electronic automatic continuously monitoring soil moisture indicator is provided having both audible and visual indicators to indicate when a plant needs moisture. The device operates by slow repetition rate short pulses of alternating voltage potential across the probes which greatly increases the life of the probes.

BACKGROUND OF THE INVENTION

This invention culminates the endeavor to design and produce a highly marketable soil moisture indicator. All previous patents covered designs such as those requiring a large battery (e.g. 9 volts) that was being continuously drained at high power requirements and thus was not designed with continuous soil moisture monitoring in mind; the units had to be first acquired with forethought, turned-on and placed into soil for a reading. Even if these units didn't have this problem, constant unidirectional current through probes such as in prior art patents would very quickly electrolysize, preventing them from remaining in soil. Even further, if this were no problem, and previous patents had incorporated alternating short duration and low frequency on the probes, as does this invention, their lack of probe plating with rhodium, chromium or some such substance to prevent quiescent corrosion is another drawback that prevents continuous in-soil resident automatic moisture monitoring and indication.

For example, one prior art patent employs bi-metallic cylindrical probes, therein described, which, if left in soil, would corrode and electrolyze, not to mention the fact of its cumbersome cord from probe to meter case assembly.

Advantages of the invention over the prior art include, small size due to integrated circuit DC/DC converter; small battery requirement due to (a) slow repetition indication occurring only during dry soil periods, (b) integrated circuit employing all transistor and function operations; resident soil operation capability due to moisture resistant conductors on printed circuit board probes and slow repetition, fast duration, alternating probe voltage pulsing; a calibrated user dial to adjust for dry indication level; a hysterysis dual trip level wherein the dry level is user adjustable and the wetness level is set, and must be reached to shut off beep/flash indication. This is in direct contrast to prior art devices which are nonautomatic in nature, requiring forethought in usage, and thus not being a plant soil fail-safe system. These prior art devices also do not have a calibrated-numbered user adjustment potentiometer to adjust the unit for different plants' soil minimum wetness levels (except for a scientific moisture content meter in one patent which incorporates a variable extremely well calibrated dial, but includes a front-end current to logarithm voltage converter and is for scientific use, and thus is a high current device not suitable for domestic and commercial usage). The prior art devices also do not include a single LED to flash on during sampling time when prior samples measured dry soil; a piezoceramic beeper to beep in unison with LED flash during dry indication; an out-of-soil automatic shut-off sensing circuit to enable a "too dry to possibly be a soil" condition for packaging and shelf life, and for plant-to-plant insertion and dryness monitoring.

BRIEF DESCRIPTION OF THE DRAWINGS

FIG. 2 is a schematic diagram of a practical circuit employed in carrying out the present invention.

DETAILED DESCRIPTION OF PREFERRED EMBODIMENTS

Figure 1:
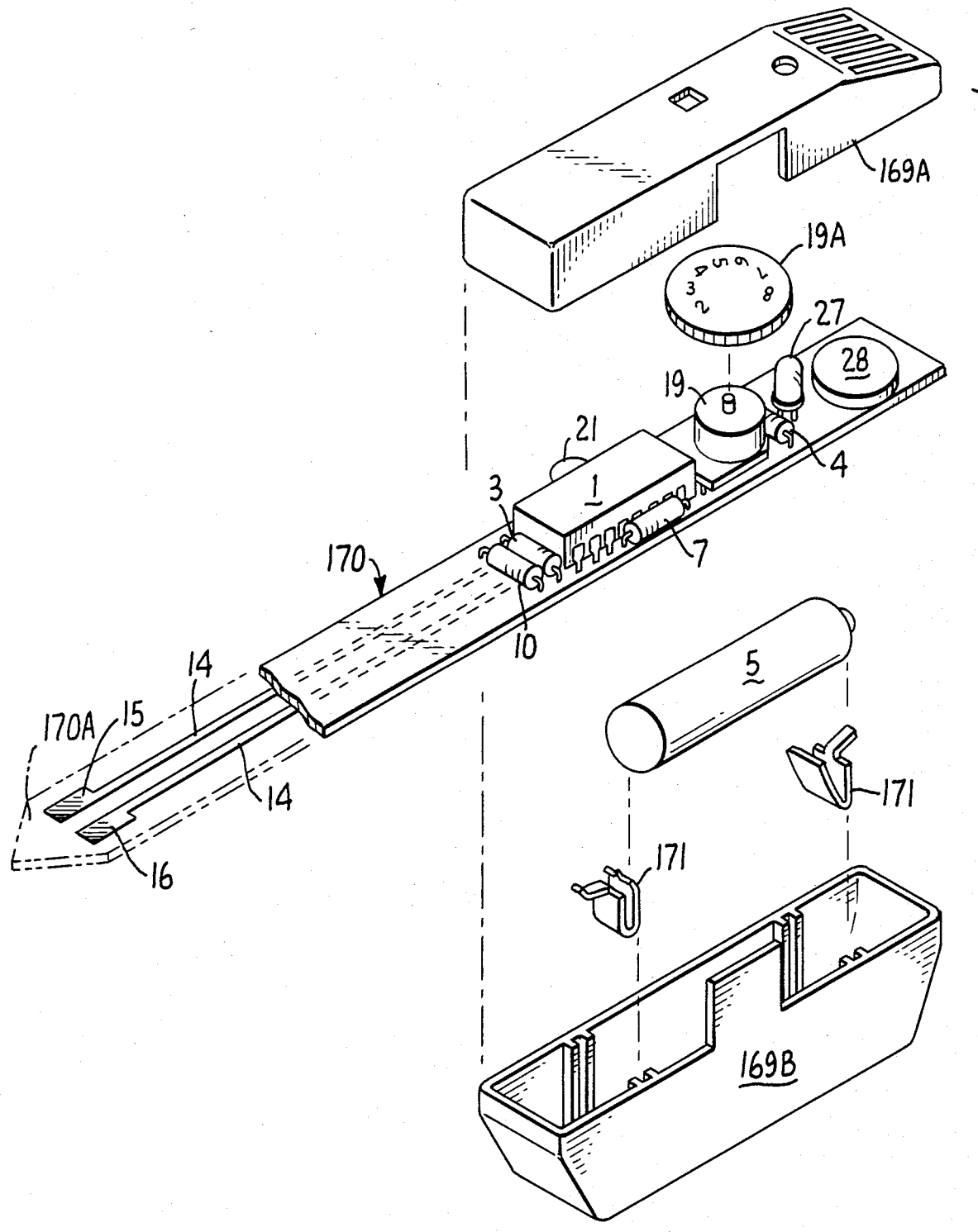
FIG. 1 is an exploded, perspective view of a moisture indicator embodying the present invention.

In the drawings like reference characters are used to identify like circuit components.

The main assemblies are shown in FIG. 1 wherein a printed circuit board 170 extends from an upper case half 169A and a lower case half 169B. Leads 14 extend from the case and terminate in the enlarged ends 15 and 16 which constitute the portion of the monitor stuck in the ground, i.e. the probe. The end 170A is sharpened for ease of insertion in soil. Also mounted on the printed circuit board are the integrated circuit 1, a potentiometer 19 with dial 19A, a LED indicator 27 and a sounder 28. These, as well as certain numbered minor components, are described in detail hereinafter. A battery 5 is mounted with clips 171 under the circuit board as shown.

In FIG. 2 those items on the integrated circuit are contained within the various boxes in dash lines while the external components, mounted on the printed circuit board, are outside the dash lines. The broad function of each of the boxes is as follows:

A: DC/DC converter
B: Bias
C: Flip-flop
D: Front end
E: Timer
F: Comparator
G: Latch
H: Output-driver The detailed function of the various components will now be described.

Related to DC/DC connector A and bias section B, external battery 5 impinges 1.5 volts across base-emitter region of transistor 58, outboard resistor 7 and transistor 54 setting up a reference bias current dependent on these devices and adjustable by resistor 7. Transistor 59 equally shares this reference current I, so each transistor 58 and 59 pass ½I while transistor 54 passes reference current I. Transistors 55, 56 and 57 mirror this current I such that their collectors sink this quantity I. Transistors 60 and 61 form the ½I source current reference, whereby 61 increases the current mirror accuracy by bypassing the base current of source current reference transistor 60 and mirror current transistors 62, 63, 64 and 65 to ground, where each mirror current ½I is sourced from both collectors of 62, 63 and 64; and the ground of this current reference and current mirror circuit section is 8, and is referred to as "ground" in subsequent description throughout.

Related to DC/DC converter section A, external capacitor 21 is used as a frequency timing adjustment, coil 4 as an energy storage device, and capacitor 3 to hold the generated increased voltage level. Sinking current I from transistor 55 is mirrored as a source current by transistor 29. Assuming transistors 44 and 45 are in cut-off (as is the case during start-up since no holding voltage is present on capacitor 3, and thus no bias through transistors 52, 53 and 48 to 45 and 44), this source current is amplified by transistor 31, then amplified by transistor 30, and then finally sourced into the bases of large geometry transistors 35 and 41, which serve as means of a switch to turn on the emitter-coupled oscillator circuit of transistors 33 and 38, and resistors 32, 34, 36 and 39. The ratios of resistors 32 and 34 to 36 and 39 is approximately five, which yields a duty cycle of 20% on the oscillator output, thereby being of appropriate optimum duty-cycle for DC/DC conversion maximum efficiency. The bases of transistors 37 and 43 receive oscillator outputs 180° out of phase with respect to each other. The transistors 40 and 42 act as a differential pair buffered by transistors 37 and 43. The condition of transistors 42 "on" and 40 "off" results in current sinking from collector of transistor 42 and level dependent by the value of coil 4 and the "on" time. During the shorter "off" duration (with respect to transistor 42), the stored energy in coil 4 is passed through diode-connected transistors 50 and 51 to raise the voltage potential of capacitor 3. When the energy from coil 4 is entirely exhausted, transistors 50 and 51 are reversed biased since the voltage (when charged up by enough oscillator cycles after start-up) on capacitor 3 is higher than the battery 5 potential. When capacitor 3 has reached a potential high enough to bias 44 and 45 "on" through diode-connected transistor 52 and zener-diode connected transistor 53 and base-emitter region of transistor 48, then the collector of transistor 44 sinks the source current from the collector of transistor 29, thereby serving as means of turning off DC/DC converter oscillator and differential stages via switching transistors 35 and 41, keeping these sections in a standby quiescent no current condition. In addition, when transistor 44 is "on," transistor 45 is also "on," and transistor 46 mirrors the collector current of transistor 45. Transistors 45 and 46 including resistor 47 form a latch that is in the above described condition qualified as "on". This latch "on" condition inverts and is an "off" condition for the oscillator and differential section via transistor 44 collector sinking current away from base of transistor 31. This latch maintains itself "on" via the feedback path transistor 45,46 and back to base of 45 by way of resistor 47. When the stored voltage on capacitor 3 has dropped sufficiently to allow the mirrored current of transistor 56 to sink the feedback current from transistor 46 via transistor 49's emitter, then the latch will turn "off", and the above described inversion occurs again whereby the oscillator and differential section turn "on."

The timer section E is initially performed by $\frac{1}{2}I$ current source from the non-reference current collector of transistor 60 into capacitor 10. This current into capacitor 10 is a slow time constant of approximately 20 seconds. When this voltage is positive enough to turn on zener-connected transistor 74, then transistor 86 turns "on," 85 reverse biases, 88 turns off and 87 forward biases to maintain 86 "on" in the flip-flop formed by 85, 86, 87 and 88. In this condition of this flip-flop, the source current of one collector of transistor 64 is amplified by current gain of transistor 87 and then by 86, whereby this collector sink current of 86 is routed through and split in half to two other collector sink paths of transistors 75 and 76, which are biased at the base by emitter of transistor 72, and whose base is biased up three diode voltages up from ground by three diode-connected transistors 69, 70 and 71. These three diodes are biased by current from I (current unit) current source of transistor 65, in addition to this source current bias are, in series, three diode-connected transistors 66, 67 and 68. The split double amplified sink current from collector of transistor 75 is amplified by pnp transistor current gain of transistor 73 and is finally connected to capacitor 10 on the emitter of transistor 73 to act as a fast (50 millisecond) voltage pull down. This "pull-down" period has occurred due to initial voltage triggering through transistor 74 and maintained by the flip-flop of devices 85, 86, 87 and 88, and this period is triggered off when the voltage on capacitor 10 has dropped to two base-emitter voltages (transistor 78 and 82) below the voltage at the base of transistor 78, which is generated by potential of six diode-connected transistors 66, 67, 68, 69, 70 and 71, by way of one collector of transistor 82 turning on transistor 88 and thus triggering the flip-flop 85, 86, 87 and 88 into the condition of 86 "off," transistor 88 "on," transistor 85 forward biased and transistor 87 reverse biased. Such a condition turns "off" the above-described "pull-down" condition, and the initial timer condition of transistor $\frac{1}{2}I$ source current of transistor 60 slowly charging the potential of transistor 10 is resumed (20 seconds time periods). During the lower potential triggering of transistor 82 "on," transistor 83 is simultaneously triggered "on" to yield two collector source currents 22 and 23, to latch section G, and the other collector source current from transistor 82 is split by transistor 77 to toggle, via lines 11, the flip-flop section C. During the pull-down period, the other half split double amplified collector sink current of transistor 76 is attenuated by a transistor current gain factor of transistor 79 to yield a sink current from the base of transistor 79 and mirrored by transistor 80 to act as a current source feedback "on" signal to transistor 162 of latch section G, and simultaneously, via transistor collector source currents (two collectors) of transistor 81, a "gate" signal and an "indicate" signal to flip-flop section C (transistor 112) and indicator section H (transistor 89), respectively.

Flip-flop section C is $\frac{1}{2}I$ current source mirror biased by transistor 62. The basic flip-flop is formed by transistors 103, 105, 106 and 108 where 103 and 108 are diode-connected and transistors 105,106 collectors are output high or low (one opposite the other) in typical flip-flop voltage states. Assuming one state of 106 "off" and 105 "on," the current from one collector of current source mirror transistor 62 is reflected through diode-connected transistor 103 and into base of transistor 105, maintaining it "on", thus the other collector source mirror current of transistor 62 is readily sinked to ground via transistor 105 making the collector of transistor 105 reverse bias diode-connected transistor 108 and keeping transistor 106 in "off" condition. Transistor 111 serves as a small capacitor for initial system turn-on such that the base of transistor 106 turns-on slower than the base of 105, and thus the initial condition of 106 "on" and 105 "off." In this condition, a "gate" signal appearing at emitter of transistor 112 is pnp-transistor-amplifier attenuated to yield a current at its base and thereafter routed to transistors 100 and 109, which "gates" mirrored transistor currents of 103 from 102 through 100 and current of transistor 108 from 110 through 109, and thus yields a gating of the high/low or low/high respective conditions of transistors 105 and 106 through 109 and 100, respectively. "Line" 11 is fed to transistors 104 and 107 which serve as a master toggle to change the high/low condition of transistors 106 and 105, respectively, to a low/high of same, respectively.

Attached to front-end section D is pair of printed circuit board traces 14 which extend out to the end of printed circuit board 170 and form probes 15 and 16 for soil moisture measurement. This front-end section has two subsections that are exact duplicates of each other except for transistor 115 and 146, thus, subsection turned "on" by transistor 113 will be described and be parenthetically referred to by its duplicate subsection turned "off" by transistor (145). The previously described flip-flop section C feeds "on" and "off" current from pair of lines 20 such that either 113 (145) or 145 (113) are "on."

This description can be viewed in the opposite state by interchanging the numbered device with the parenthetically numbered device. When 113 (145) is "on" and mirroring current, 119 (140), 120 (139), and 125 (133) are mirroring the same current on a per collector basis, where transistors 125 (133) have both collectors tied together to yield twice the mirrored current quantity. Unit quantity of mirrored current from collector of transistor 113 (145) is transistor current gain amplified by 114 (144) to maintain transistor 118 (143) in a saturated "on" condition, the emitters of which are biased one diode voltage up from ground by diode-connected transistor 115. One collector mirror current of transistor 119 (140) is transistor current gain amplified by transistor 116 (141) and emitter fed to resistor 117 (142) yielding voltage-drop of $$I\beta R_{117(142)}$$

where I is one mirror current unit and $\beta$ is transistor current gain. The potential at the bottom of resistor 117 (142) is the diode voltage of transistor 115 and the saturation voltage of transistor 118 (143):

$$VD_{115} + VSAT_{118(143)}$$

which is connected to probe 16 (15) since transistor 130 (129) and 131 (128) are "off." The unit mirror collector currents from 119 (140) and dual collector mirror current from 125 (133) biases the op-amp composed of transistors 121 (138), 122 (137), 123 (136), 124 (135), 126 (134), 128 (131), and 129 (132), which drives emitters of 128 (131) and 129 (130) to the same potential as that at the top of resistor 117 (142) since the base of transistor 121 (138) is the op-amp positive input and the base of 122 (137) is the negative input of the op-amp that is connected to the op-amp emitter drive outputs of transistors 128 (131) and 129 (130). This total potential is $$VD_{115} + VSAT_{118(143)} + I\beta R_{117(142)}$$

which is connected to probe 15 (16). The potential difference between probe 15 (16) and 16 (15) is the difference between the last two voltage expressions, and is equal to the first voltage expression, that potential voltage drop across resistor 117 (142)

$$I\beta R_{117(142)}$$

The resultant total current from collectors 128 (131) and 129 (130) is the voltage potential across the probes 15 and 16 divided by the soil resistance seen by these probe surfaces:

$$\frac{I\beta R_{117(142)}}{R_{soil}}$$

One half of this total current is one collector's sink current and is the current line 17 fed to the bottom of customer dryness level potentiometer adjustment 19, to which potentiometer is biased on the top by transistor 146 receiving one collector mirror bias current from transistor 120 (139) and transistor current gain multiplying to yield a voltage potential across resistor of $$I\beta R_{147}$$

The line 17 moisture-indicative current sinked from the bottom of potentiometer 19 yields a potential drop across it of:

$$\frac{I\beta R_{117(142)}}{2 R_{soil}} R_{19}$$

All the above section D events occur during the "sampling" period down-ramp of timing capacitor 10, about 50 milliseconds.

In the current comparator section F, resistor 147 is two diode voltages, diode-connected transistors 148 and 149, above a common voltage node of comparator transistors 149, 153 and 154. This potential is added to resistor 147 potential yielding $$2VD + I\beta R_{147}$$

at the top of resistor 147 which is also connected to the top of user dryness adjustment potentiometer 19. Transistors 152, 153 biased "on" or "off" dictate the possible outputs states of collector outputs transistor 153 (output line 22) and transistor 154 (output line 23). The expression for the based-emitter voltage potentials of transistors 152 and 153 can be set equal to the potential at the bottom of user dryness adjustment potentiometer 19 to yield a switching threshold expression.

$$2VD + I\beta R_{147} - \frac{I\beta R_{117(142)}}{2 R_{soil}} R_{19} = 2V_{BE}$$

In the typical circuit, $R_{117(142)} = 40$ k$\Omega$ and $R_{147} = 60$ k$\Omega$. By arranging the expression and subtracting the diode voltages yields $$I\beta R_{117(142)} K \left(1 - \frac{R_{19}}{2K R_{soil}}\right) = 2V_{BE} - 2VD$$

where $K = \frac{R_{147}}{R_{117(142)}}$ which is $K = 3/2$ for typical circuit values. The 2VBE−2VD value is approximately minus 0.3 volts, due to current biasing differences. The purpose is to have the "trip" value dependent on the ratio of soil resistance (Rsoil) to the user potentiometer adjustment 19 and not dependent on the integrated circuit resistors 147, 117 and 142 (or any circuit parameters), which is seen to be achieved when examining the parenthetical expression $$\left(1 - \frac{R_{19}}{2KR\text{soil}}\right)$$

for typical circuit values $R_{19} = 5$ M$\Omega$ and a corresponding soil resistance $R\text{soil} = 1$ M$\Omega$ where $2K = 3$ yielding the expression somewhat negative to account for the slight negative value of expression $2V_{BE} - 2V_D$, but to which primarily demonstrates this major dependence on the ratio of resistor 19 to the resistance of the soil medium.

The resultant output at line 22 and 23 are "strobed" up to their opposite respective values by current source strobbing collectors of transistor 83 at the end of the previously mentioned "sample" period when capacitor 10 is down-ramped to the most negative potential possible on it. When the soil is dryer than the potentiometer 19 user adjustment value, 22 is "low" and 23 is "high" when strobbed. When the soil is wetter than the potentiometer 19 value, 22 is "high" and 23 is "low". These two opposite outputs, 22 and 23, are connected to the latch section G, specifically to transistor 157 and 160 respectively. Thus latch section G is slaved to an appropriate state by prior current comparator strobe outputs 22 and 23 during "strobe" cycle and remaining "latched" in this condition due to flip-flop means of transistors 155, 156, 157, 158, 159 and 160, 161. The latch has two current-mirror source sustaining currents from the collectors of transistor 63. Transistors 157 and 160 act as means of basic flip-flop "on" or "off" outputs, where they would be respectively opposite, and diode-connected transistors 161, 155 along with transistors 158 and 159 as a diode steering for the flip-flop. During conditions of wet soil that is wetter (smaller Rsoil) than the user adjustment dryness level of potentiometer 19, line 22 would strobe transistor 157 "on", thus latching up the latch into a state of 161 forward biased, transistors 155, 158 and 159 reverse biased, and 160 "off". During conditions of dry soil that is dryer (larger Rsoil) than the user adjustment dryness level of potentiometer 19, line 23 would strobe transistor 160 "on" and 157 "off", thus 161 would be reverse biased and 155, 158 and 159 forward biased.

This last condition is the major condition whereby the overall unit is to indicate by way of LED 27 and piezoelectric ceramic beeper 28 that water is needed in the soil moisture medium. This is done by yielding transistor current amplified base current from transistors 155 and 156 at collector of transistor 158, which is line 25. This line goes into the indicator section H. During this indication "on" cycle, transistor 156 mirrors one sink unit of bias current I that is sinked through transistor 155. This collector sink current of transistor 156 is mirrored by transistor 84 in the Timer section E to add another source current unit I to the existing quiescent source current I of transistor 60. Thus, the 20 second timing on capacitor 10 is halfed to 10 seconds during indication cycle to have an appropriate indication rate. In addition, during indication cycle, transistor 159 mirrors transistor 158 current, which is biased "on" by transistor 162 during sampling periods and then divided in half by transistors 163 and 164, to which is diode dropped by diode connected transistor 165. This halfed current at the collector of transistor 164 is mirrored by transistor 166 and serves as a feedback current to the soil moisture indicative current on line 17 (bottom of potentiometer 19), and is thus the hysterysis change of threshold current that the wetness soil moisture resistance must reach before the unit can "trip" "off" the indication cycle, to which value corresponds to approximately the highest wetness (or lowest dryness) value of potentiometer 19.

The other half of soil moisture current represented by expression $$\frac{I\beta\, R117\,(142)}{2\, R\text{soil}}$$

from collector 129 (130) is sinked out of the base of transistor 167, turning it "on" in a saturated condition and being sink current biased by transistor 57. When there is no soil medium present, no base current of transistor 167 results, and thus transistor 168 mirrors the collector current of 57 to the base of transistor 172 to force the I comparator F into a pseudo-wet cycle whereby no indication cycle of the overall unit can occur when unit is not in a soil medium of some reasonable Rsoil resistance value.

Indicator section H has attached to it LED 27 and piezoelectric ceramic beeper 28 which are simultaneously turned "on" by the "and"-ing function of transistor 89, which must receive a bias on its base from one collector of transistor 81 during sample time and an indication-cycle "on" sink current on its emitter from the collector of transistor 158. This condition being met, the difference of the currents will pass on to the base of the transistor 90 to turn it "on." One collector is connected to the base of transistor 91, which transistor current gain amplifies and connects this current to inverted npn transistor 92, to which is connected the LED device 27. The potential across the LED is the battery voltage of battery 5 minus the saturation voltage of transistor 92. The other collector of transistor 90 connects to the base of transistor 93 and is therein used as a saturated biasing means for transistors 95 and 99 through resistor 94. This biased input on the base of transistors 95 and 99 serves as the beeper feedback input which is connected to the beeper (28), feedback tab for self-resonant operation of said beeper. The positive beeper output is the emitter of transistor 98, which is biased by resistor 100 and driven by transistor 96 via the collector current of transistor 95. The negative beeper output is connected to the collector of transistor 99 which is biased by resistor 97 and driven at the base directly by the feedback tab of beeper 28.

Many variations can be made in the structure shown without departing from the spirit of this invention. For instance, other audible or visual outputs could be used. Also instead of a single I.C. illustrated, the device could be made from discrete components or a combination of standard I.C.'s and/or discrete components.

We claim:
1. An automatic continuously monitoring soil moisture monitor/indicator comprising a circuit containing:
   a. outputs connected to an internal means for alternately pulsing external probes in equal and opposite voltage polarities,
   b. means for pulsing a specific voltage across said probe connection output during either polarity sampling cycle,
   c. an output means connected to a capacitor whereby said capacitor integrates for sampling rate and duration time, d. means for yielding absolute value of current from said probes to an output connection such that said current from said probes proportionately appears at said output connection for attachment to a user adjustment potentiometer, e. means for voltage comparison yielding "on" or "off" result from said voltage comparison, where said voltage comparison is a function of the ratio of soil moisture dependent resistance and said user adjustment potentiometer resistance, f. means for latching and holding "on" or "off" condition at end of sampling period, and g. means of turning on an output indicating device through output connection if latched condition is "on" during sampling period.

2. A soil moisture indicating device containing the system of claim 1 and further comprising a. a printed circuit board containing said integrated circuit of claim 1, said timing capacitor and said adjustment potentiometer, and b. a pair of printed circuit board traces which widen to "probe" pads having corrosive resistant plating means.

3. As a soil moisture indicating device containing the system of claim 2 and further comprising a case to enclose said printed circuit board, said integrated circuit, said timing capacitor and said user adjustment potentiometer, with said probe pads extending from the case.

4. A soil moisture indicating device containing the system of claim 2 and further comprising the addition of a case to enclose said printed circuit board and associated equipment with probes extending from said case.

5. A soil moisture indicating device containing the system of claim 2 and further comprising one LED connected to said indicating output connection of said integrated circuit.

6. A soil moisture indicating device containing the system of claim 5 and further comprising one beeper, connected to said integrated circuits input and outputs whereby internal means exists to oscillate and "beep" said beeper in unison with said LED's activation during said sampling period.

7. A soil moisture indicating device containing the system of claim 2 and further comprising one piezoelectric ceramic beeper connected to said integrated circuit's input and outputs whereby internal means exists to oscillate and "beep" said beeper in unison with said LED's activation during said sampling period.

8. A soil moisture indicating device containing the system of claim 3 and further comprising one LED connected to said indicating output connection of said integrated circuit.

9. A soil moisture indicating device containing the system of claim 8 and further comprising one beeper connected to said integrated circuit's input and outputs and internal means to oscillate and "beep" said beeper in unison with said LED's activation during said sampling period.

10. A soil moisture indicating device containing the system of claim 3 and further comprising one piezoelectric ceramic beeper connected to said integrated circuit's input and outputs whereby internal means exists to oscillate and "beep" said beeper in unison with said LED's activation during said sampling period.

11. A soil moisture indicating device of claim 10 including a DC to DC converting circuit with a coil and capacitor.

12. A soil moisture indicating device containing the system of claim 1 and further comprising a. connections to said integrated circuit for two capacitors and one coil whereby internal circuit means yields a DC to DC conversion using these external devices, and thus enabling operation from a small low voltage battery whereby the overall unit physical dimensions are small.

13. The soil moisture indicating device of claim 12 having the following additional structure a. a printed circuit board, a timing capacitor and an adjustment potentiometer, and b. a pair of printed circuit board traces which widen to "probe" pads having a corrosion resistant metal thereon.

14. An automatic continously monitoring soil moisture monitor/indicator comprising a circuit containing:

a. outputs connected to an internal means for pulsing external probes in equal sampling voltage pulses, b. means for pulsing a specific voltage across said probe connection output during a sampling cycle, c. an output means connected to a capacitor whereby said capacitor integrates for sampling rate and duration time, d. means for yielding absolute value of current from said probes to an output connection such that said current from said probes proportionately appears at said output connection for attachment to a user adjustment potentiometer, e. means for voltage comparison yielding "on" or "off" result from said voltage comparison, where said voltage comparison is a function of the ratio of soil moisture dependent resistance and said user adjustment potentiometer resistance, f. means for latching and holding "on" or "off" condition at end of sampling period, and g. means of turning on an output indicating device through output connection if latched condition is "on" during sampling period.

15. A soil moisture indicating device containing the system of claim 14 and further comprising a. a printed circuit board containing said integrated circuit of claim 1, said timing capacitor and said adjustment potentiometer, and b. a pair of printed circuit board traces which widen to "probe" pads having corrosive resistant plating means.

* * * * *